US009387288B2

(12) United States Patent
Karratt et al.

(10) Patent No.: US 9,387,288 B2
(45) Date of Patent: Jul. 12, 2016

(54) DOSAGE SENSING UNIT WITH TACTILE FEEDBACK

(71) Applicant: CALIBRA MEDICAL, INC., Redwood City, CA (US)

(72) Inventors: Joseph M. Karratt, Redwood City, CA (US); Brett Cross, Seattle, WA (US)

(73) Assignee: Calibra Medical, Inc., Redwood City, CA (US)

( * ) Notice: Subject to any disclaimer, the term of this patent is extended or adjusted under 35 U.S.C. 154(b) by 127 days.

(21) Appl. No.: 14/075,269

(22) Filed: Nov. 8, 2013

(65) Prior Publication Data

US 2014/0074019 A1 Mar. 13, 2014

Related U.S. Application Data

(62) Division of application No. 12/263,921, filed on Nov. 3, 2008, now Pat. No. 8,613,719.

(51) Int. Cl.
*A61M 31/00* (2006.01)
*A61M 5/142* (2006.01)
*A61M 5/168* (2006.01)
*G08B 6/00* (2006.01)

(52) U.S. Cl.
CPC ........ *A61M 5/14248* (2013.01); *A61M 5/16831* (2013.01); *A61M 5/16881* (2013.01); *G08B 6/00* (2013.01); *A61M 2205/3317* (2013.01); *A61M 2205/3331* (2013.01); *A61M 2205/502* (2013.01); *A61M 2205/52* (2013.01); *A61M 2205/582* (2013.01); *A61M 2205/583* (2013.01)

(58) Field of Classification Search
CPC ..................... A61M 5/14248; A61M 5/16831; A61M 2205/3317; A61M 2205/3331; A61M 2205/502; A61M 2205/52; A61M 2205/582; A61M 5/16881
See application file for complete search history.

(56) References Cited

U.S. PATENT DOCUMENTS

| 4,522,213 | A | 6/1985 | Wallroth et al. |
|---|---|---|---|
| 5,317,506 | A | 5/1994 | Coutre et al. |
| 5,547,470 | A | 8/1996 | Johnson et al. |
| RE38,189 | E | 7/2003 | Walker et al. |
| 7,038,192 | B2 | 5/2006 | Lu et al. |
| 7,981,102 | B2 | 7/2011 | Patel et al. |
| 2003/0217772 | A1 | 11/2003 | Lu et al. |
| 2004/0167464 | A1 | 8/2004 | Ireland et al. |
| 2007/0149926 | A1 | 6/2007 | Moberg et al. |
| 2008/0167641 | A1 | 7/2008 | Hansen et al. |
| 2009/0088689 | A1 | 4/2009 | Carter |
| 2009/0088694 | A1 | 4/2009 | Carter |
| 2009/0221957 | A1 | 9/2009 | Bowman et al. |
| 2009/0326472 | A1 | 12/2009 | Carter |

OTHER PUBLICATIONS

International Search Report and Written Opinion issued in related International Application No. PCT/US2009/062731, mailed Aug. 19, 2010, 12 pages.

*Primary Examiner* — Rebecca E Eisenberg (57) ABSTRACT

A drug infusion assembly comprises a drug delivery device arranged to adhere to a patient's skin and includes a reservoir that holds the drug, a cannula that delivers the drug to the patient, and a pump that causes the drug to flow to the cannula. The assembly further includes a monitor device for providing information about the operation of a drug delivery device. The monitor device includes a housing arranged to be attached to and detached from the drug delivery device, a sensor that senses the operation of the drug delivery device and generates an activation signal, a clock mechanism that generates a time signal, a memory that receives and stores the activation signal and the time signal and creates an information packet coordinating the time signal and the activation signal, an interrogator that interrogates the memory such that the memory generates a memory signal in response thereto, and a responder that receives the memory signal and generates a response.

8 Claims, 10 Drawing Sheets

DOSAGE SENSING UNIT WITH TACTILE FEEDBACK

CROSS-REFERENCE TO RELATED APPLICATION

This application is a Divisional Patent Application of Utility application Ser. No. 12/263,921, filed on Nov. 3, 2008, the contents of which are relied upon and incorporated by reference.

BACKGROUND OF THE INVENTION

The present invention relates to a device for sensing medicament dosing in a drug infusion set. In some embodiments it also includes the ability to retain and recall dosing history and to provide tactile feedback to a user reflecting recent dosing activity. In some embodiments it also includes the ability to retain and dosing history and to provide a download of that history to an electronic device such as a computer or a similar device specifically for that purpose.

The invention relates to a sensing device that is applicable to infusion devices for liquid medicaments in general, but for purposes of example, the use of the device in connection with disposable infusion devices for the administration of insulin in diabetes is described below.

Glucose is the central source of energy in the human body, and is generated by the digestion of the food, particularly carbohydrates and released into the bloodstream for distribution throughout the body. Insulin is a hormone that allows the glucose in the bloodstream to be absorbed by the cells of the body. A healthy person makes enough insulin for the body's cells to absorb essentially all the glucose generated by the food that the body digests. Insulin is produced in the pancreas and released into the bloodstream and is present at a low basal level at all times, but is sometimes released in larger bolus amounts in response to or anticipation of a person's intake of carbohydrates, for example at a meal.

Diabetes is a disorder of the manufacture and utilization of insulin. It is a huge and growing health problem among virtually all segments of the population. It is an incurable and progressive disease that typically manifests itself in one of two different ways, type 1 diabetes (T1) and type 2 diabetes (T2). In T1 diabetes the patient loses the ability to make insulin at all, generally as a result of destruction of cells of the pancreas. This often happens early in life and was previously sometimes called early onset diabetes. With this type of diabetes, insulin replacement therapy is necessary, and without the administration of insulin the patient dies.

In T2 diabetes, the patient develops an inability to use insulin efficiently. Often diet and exercise will delay progression, but the disease typically progresses to the stage where it is necessary to administer drugs to increase the body's production of insulin or the efficiency of use of the insulin present. At some point thereafter, the disease usually progresses to the point that insulin injections are required.

In both T1 and T2 where insulin injections are required, careful monitoring of the amount and timing of injections is important. Certain insulin analogs have been developed that allow a single or perhaps two daily injections to provide the rough equivalent of the daily basal insulin of a patient without diabetes. However, mimicking the body's bolus insulin amounts is far more delicate. Bolus administrations of insulin are typically given about half an hour before a meal. The amount of insulin that is appropriate varies from one administration to the next depending on the amount and type of the food to be eaten, the amount of exercise that the patient has recently engaged in, the how tired the patient is, and any number of other factors.

Recent treatment protocols are trending toward a move to earlier treatment of T2 diabetes with insulin, and in more precise and constant monitoring of the blood glucose level of the patient. This protocol is sometimes referred to as Intense Insulin Therapy, or IIT and involves the administration of insulin three or more times per day, or constant administration by a pump. As a result, in addition to the growing problem of diabetes in the population, it is likely that in the future a larger portion of people with diabetes will be treated by the administration of insulin, and IIT will become far more common.

Administration of insulin has traditionally been accomplished using a syringe. Recently, needle carrying pen-like devices have also been employed for this purpose. Both forms of insulin administration require the patients to stick themselves each time they inject insulin, often many times a day. Additionally, the act of injecting themselves or having a helper inject them is socially awkward for the person with diabetes. Thus, these traditional forms of insulin administration have been a rather pervasive intrusion in the lives and routines of the patient's who have had to adopt and employ them. If the social awkwardness results in a patient skipping administrations, that may be detrimental to control of the disease.

More recently, insulin pumps attached by tubing to an infusion set mounted on the patient's skin have been developed as an alternative form of insulin administration. Such pumps may be controlled by a programmable remote electronic system employing short range radio communication between a control device and electronics that control the pump. While such devices may involve fewer needle sticks, they are expensive to manufacture, complex to operate and cumbersome and awkward to wear. Further, the cost of such devices can be many times the daily expense of using a traditional injection means such as a syringe or an insulin pen.

Devices of the type mentioned above also require a significant amount of training to control and use. Great care in programming the devices is required because the pumps generally carry sufficient insulin to last a few days and improper programming or operation of the pumps can result in delivery of an excessive amount of insulin which can be very dangerous and even fatal.

Many patients are also reluctant to wear a pump device because they too are generally socially awkward. The devices are generally quite noticeable and can be as large as a pager. Adding to their awkwardness is their attachment to the outside of the patients clothes and the need for a catheter like tubing set running from the device to an infusion set located on the patient's body. Besides being obvious and perhaps embarrassing, wearing such a device can also be a serious impediment to many activities such as swimming, bathing, athletic activities, and activities such as sun bathing where portions of the patient's body are necessarily uncovered.

In view of the above, a more cost effective and simple device has been proposed whereby an injection system is discreetly attached directly to the skin of the patient. The device may be attached to the patient under the patient's clothing to deliver insulin into the patient by the manual pumping of small doses of insulin out the distal end of a temporarily indwelling cannula that is made a part of the pump device. The cannula may be made a part of the drug delivery device before, during or after the attachment of the drug delivery device to the skin of the patient. The device may be made quite small and, when worn under the clothes, entirely unnoticeable in most social situations. It may still carry sufficient insulin to last a patient several days. It can be colored to blend naturally with the patient's skin color so as not to be noticeable when the patient's skin is exposed. As a result, insulin for several days may be carried by the patient discreetly, and conveniently applied in small dosages after only a single needle stick. For a more complete description of devices of this type, reference may be had to co-pending application Ser. No. 11/906,130, filed on Sep. 28, 2007 for DISPOSABLE INFUSION DEVICE WITH DUAL VALVE SYSTEM, which application is owned by the assignee of this application and hereby incorporated herein by reference in its entirety.

As noted above, current medical protocol is trending toward IIT where frequent and precise insulin administration is used. Also as noted above, each bolus insulin dosage is unique and will vary from one to the next. It is therefore very important to keep track of the timing and amount of each dosage. Patients are often advised to keep journals whereby they record each insulin administration and their blood glucose in frequent intervals to help carefully monitor their treatment.

Where the administration of the dose of insulin involves loading a syringe or dialing an amount on an insulin pen, and injecting oneself with the dose, the patient is unlikely to forget that they had administered the dose or the amount of the dose. Likewise if a complex electronic unit is controlling an insulin pump, one of its electronic functions can be to recall each dose and display the results on the individual remote unit. However, the very simple and discreet nature of the disposable unit described above makes it more likely that the patient may not remember the details of the last insulin administration. The fact that the device is worn on the patient's body in an unobtrusive manner also makes a visual display less useful. It is very likely that the patient will be wearing the device where they cannot easily see it. Finally, in furtherance of the goal of making the treatment less of an unpleasant intrusion into the daily life of the patient, it would be helpful to have a means of keeping a record of insulin treatment without the need to carry and maintain a journal.

Thus there is a need for a sensing device for use with an attached drug delivery device that can sense dosing by that device, and respond to a query from a user with information regarding recent dosing activity. There is a need for such a device that can provide that response in a tactile form that may be sensed by the user without the need to see the sensing device. There is a need for such a device to be discreet to be consistent with the ability of such a drug delivery device to be discreet and unobtrusive. Finally it would be useful if such a device could store the history of the insulin administration over a significant period of time and provide that information later to a physician or patient.

As mentioned previously, the administration of insulin is used here for exemplary purposes. However the administration of any liquid medicament, particularly where relatively frequent or constant administration is indicated, would be greatly aided by this invention. For example, where administration of pain medication for a chronic situation is required, an unobtrusive infusion device would be helpful, and a method of sensing and later providing information concerning recent dosing or long term dosing history would be very helpful. In some chemotherapeutic regimes, a similar system would be very useful. The invention is not limited by the exemplary method described herein except as explicitly stated in the claims.

SUMMARY OF THE INVENTION

In one embodiment, the invention provides a monitoring device for providing information about the operation of a drug delivery device. The monitoring device comprises a housing arranged to attach to the drug delivery device, a sensor that senses the operation of the drug delivery device and provides operational data indicative of the operation of the drug delivery device, a memory that stores the operational data, and an indication generator that generates a perceptible indication of the operational data.

The indication generator may be arranged to provide a tactile response to provide the perceptible indication. The tactile response may be a vibratory response. The indication generator may be a motor. The motor may be an electric motor.

The sensor may comprise an optical sensor and/or a magnetic sensor. The drug delivery device may include a pump that delivers the drug to a patient. For example, the pump may be a mechanical stroke pump and the sensor may sense the strokes of the pump. The monitoring device may further comprise a timer that times a dosing session of the device.

The drug delivery device may include at least one valve. The operation of the drug delivery device initiates with operation of the at least one valve and the magnetic sensor senses the operation of the at least one valve. The optical sensor senses strokes of the pump.

The memory may store each pump stroke occurring during a dosing session. The indication generator may generate a perceptible indication of the number of pump strokes occurring during a last dosing session. The memory may store operational data for a number of dosing sessions in a history file. The monitoring device may further include an interface arranged to provide the history file to an external reader. The interface may comprise a USB interface.

In another embodiment, a monitor device provides information about the operation of a drug delivery device. The monitor device comprises a sensor that senses the operation of the drug delivery device and generates an activation signal, a clock mechanism that generates a time signal, a memory that receives and stores the activation signal and the time signal and creates an information packet coordinating the time signal and the activation signal; an interrogator that interrogates the memory such that the memory generates a memory signal in response thereto, and a responder that receives the memory signal and generates a tactile response.

In another embodiment, a monitor device provides information about the operation of a drug delivery device. The drug delivery device includes a mechanical stroke pump that delivers the drug to a patient and at least one valve, the operation of which initiates operation of the drug delivery device. The monitor device comprises a housing arranged to attach to the drug delivery device, a timer that times a dosing session, a magnetic sensor that senses the operation of the at least one valve, an optical sensor that senses operation of the pump to provide operational data, a memory that stores the operational data provided by the optical sensor during a last dosing session, an interrogator that interrogates the memory such that the memory generates a memory signal in response thereto representing operation of the drug delivery device during a last dosing session, and a responder that receives the memory signal and generates a tactile response.

In a further embodiment, a drug infusion assembly comprises a drug delivery and a monitor device. The drug delivery device is arranged to adhere to a patient's skin and includes a reservoir that holds the drug, a cannula that delivers the drug to the patient, and a pump that causes the drug to flow to the cannula. The monitor device provides information about the operation of the drug delivery device. The monitor device comprises a housing arranged to be attached to and detached from the drug delivery device, a sensor that senses the operation of the drug delivery device and provides operational data indicative of the operation of the drug delivery device, a memory that stores the operational data, and an indication generator that generates a perceptible indication of the operational data.

In a still further embodiment, a drug infusion assembly comprises a drug delivery device arranged to adhere to a patient's skin and includes a reservoir that holds the drug, a cannula that delivers the drug to the patient, and a pump that causes the drug to flow to the cannula. The assembly further includes a monitor device for providing information about the operation of a drug delivery device. The monitor device includes a housing arranged to be attached to and detached from the drug delivery device, a sensor that senses the operation of the drug delivery device and generates an activation signal, a clock mechanism that generates a time signal, a memory that receives and stores the activation signal and the time signal and creates an information packet coordinating the time signal and the activation signal, an interrogator that interrogates the memory such that the memory generates a memory signal in response thereto, and a responder that receives the memory signal and generates a response.

BRIEF DESCRIPTION OF THE DRAWINGS

The features of the present invention which are believed to be novel are set forth with particularity in the appended claims. The invention, together with further features and advantages thereof, may best be understood by making reference to the following description taken in conjunction with the accompanying drawings, in the several figures of which like reference numerals identify identical elements, and wherein:

DETAILED DESCRIPTION OF THE INVENTION

Figure 1:
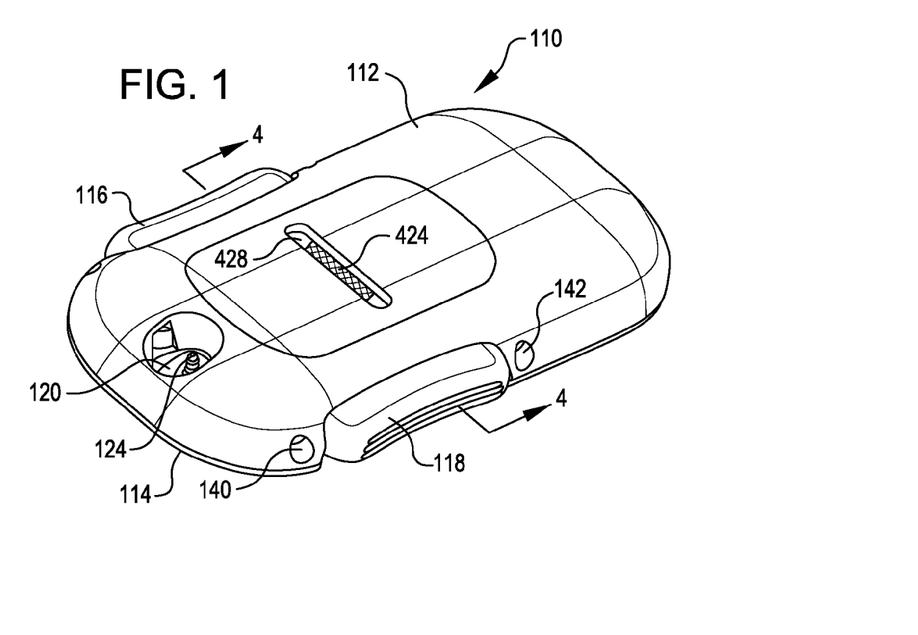
FIG. 1 is a perspective view of an infusion device which may be employed in an assembly embodying the present invention.
Figure 2:
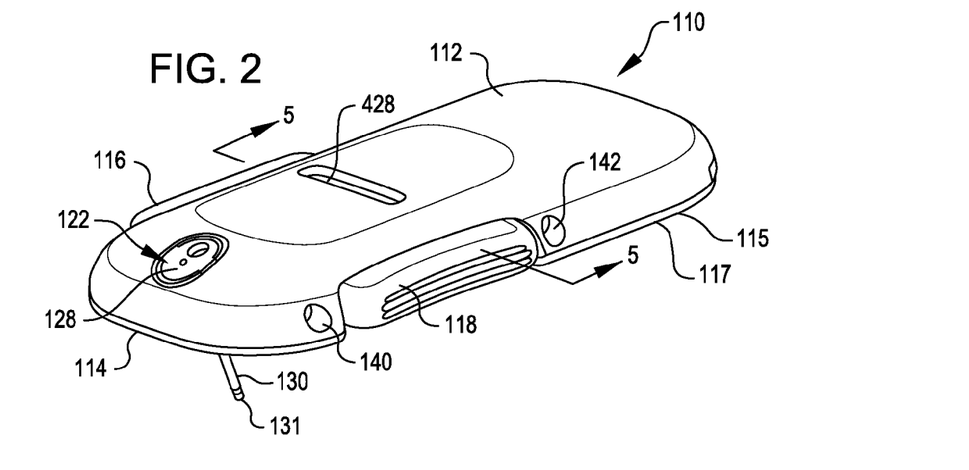
FIG. 2 is another perspective view of the infusion device of FIG. 1 shown with a deployed cannula.

Referring now to FIGS. 1 and 2, they are perspective views of an infusion device 110 which may be used in an assembly embodying various aspects of the present invention. More particularly, the device 110 may receive a monitoring device thereon embodying the present invention and described subsequently to form an infusion assembly capable of providing a drug, such as insulin, to a patient and to report to the patient information pertaining to the drug delivery.

FIG. 1 shows the device prior to receiving and thus without a cannula while FIG. 2 illustrates the device after having received a cannula 130 that has a distal end 131. As may be seen in both FIGS. 1 and 2, the device 110 generally includes an enclosure 112, a base 114, a first actuator control button 116, and a second actuator control button 118.

The enclosure 112, as will be seen subsequently, is formed by virtue of multiple device layers being brought together. Each layer defines various components of the device such as, for example, a reservoir, fluid conduits, pump chambers, and valve chambers, for example. This form of device construction results in a compact design and enables manufacturing economy to an extent that the device is disposable after use.

The base 114 preferably includes a pad 115 attached to the base 114. The pad 115 has an adhesive coating 117 on the side thereof opposite the base 114 to permit the device to be adhered to a patient's skin.

The device 110, as will be seen herein after is first adhered to the patient's skin followed by the deployment of the cannula 130 thereafter. However, it is contemplated herein that various aspects of the present invention may be realized within a device that may alternatively be mated with a previously deployed cannula assembly.

The actuator buttons 116 and 118 are placed on opposites sides of the device 110 and directly across from each other. This renders more convenient the concurrent depression of the buttons when the patient wishes to receive a dose of the liquid medicament contained within the device 110. This arrangement also imposes substantially equal and opposite forces on the device during dosage delivery to prevent the device from being displaced and possibly stripped from the patient. As will be further seen hereinafter, the concurrent depression of the buttons is used to particular advantage. More specifically, the actuator button 116 may serve as a valve control which, when in a first position as shown, establishes a first fluid path between the device reservoir and the device pump to support pump filling, and then, when in a second or depressed position, establishes a second fluid path between the device pump and the device outlet or distal end of the cannula to permit dosage delivery to the patient. As will be further seen, a linkage between the control actuator buttons 116 and 118 permits actuation of the device pump with the actuator control button 118 only when the second fluid path has been established by the first actuator control button 116. Hence, the first actuator control button 116 may be considered a safety control.

The actuator buttons 116 and 118 are preferably arranged to require a complete through of their travel to achieve activation of the device pump and thus dosage delivery. This, together with the sudden release of resistance to actuator advancement creates a snap action that provides an advantage in positively knowing that dosage delivery has occurred and that no less than a full dose has been delivered. For more description regarding this feature, reference may be had to co-pending application Ser. No. 11/906,102, titled DISPOSABLE INFUSION DEVICE WITH SNAP ACTION ACTUATION, which application is owned by the assignee of this application and is incorporated herein by reference in its entirety.

As may be noted in FIG. 1, the device 110 includes a cavity 120 that is arranged to receive a cannula assembly 122 (FIG. 2) from which the cannula 130 extends. When the cannula is deployed, the outlet 124 of the device 110 is placed in fluid communication with the cannula 130 by a cannula carrier 128 of the cannula assembly 122 that carries the cannula. When thus deployed, the cannula 130 extends from the base 114 of the device 110 to beneath the skin of the user.

As may further be noted in FIGS. 1 and 2, the enclosure 112 of the device 110 includes a pair of pockets 140 and 142 on opposite sides of the second actuator button 118. A similar pair of pockets, not seen in the figure, are also provided on opposite sides of the first actuator button 116. These pockets are used to receive corresponding projections of a cannula placement assembly for releasably joining the cannula placement assembly to the device 110 to support cannula deployment as will be described subsequently. Such a cannula placement assembly is fully described in co-pending application Ser. No. 12/147,295, filed on Jun. 26, 2008 for DISPOSABLE INFUSION DEVICE WITH AUTOMATICALLY RELEASABLE CANNULA DRIVER, which application is owned by the assignee of the present invention and hereby incorporated herein by reference. As described therein, upon cannula deployment, the cannula placement assembly is automatically released from the device by the driver projections being forced from the pockets.

Figure 3:
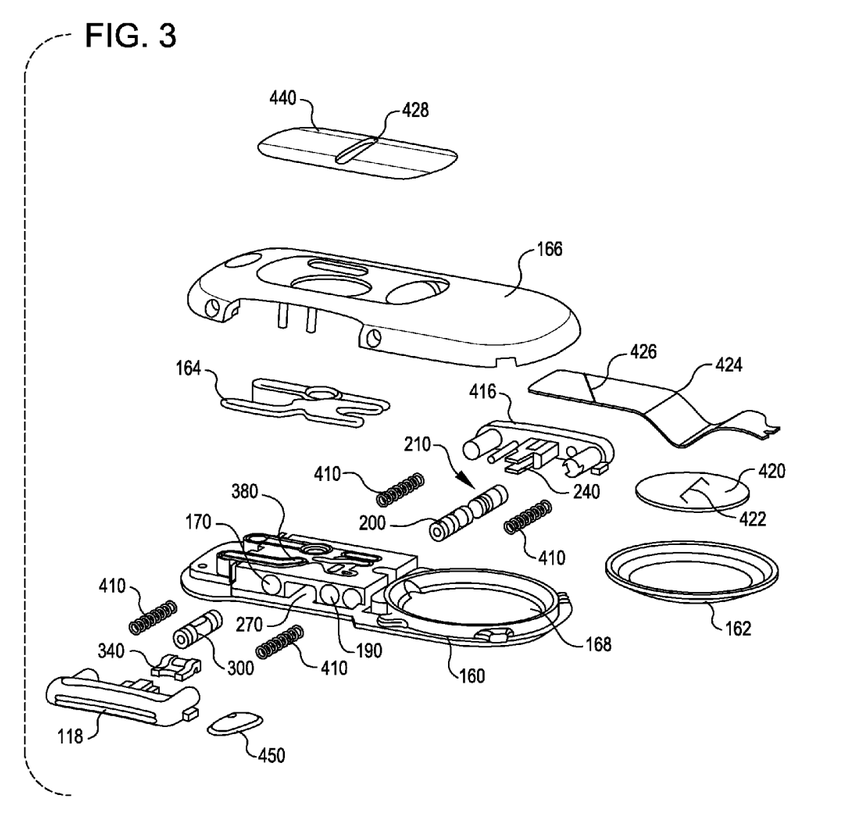
FIG. 3 is an exploded perspective view of the device of FIG. 1.

Referring now to FIG. 3, it is an exploded perspective view of the device 110 of FIG. 1. It shows the various component parts of the device. The main component parts include the aforementioned device layers including the base layer 160, a reservoir membrane 162, an intermediate layer 164 and a top body layer 166. As may also be seen in FIG. 3, the base layer 160 is a substantially rigid unitary structure that defines a first reservoir portion 168, a pump chamber 170, and a valve chamber 190 that receives a shuttle bar 200 of a shuttle valve 210. A reservoir membrane layer 162 is received over the reservoir portion 168 to form an expandable/deflatable reservoir of the device 110. The base layer 160 may be formed of plastic, for example. The base and the top body layer may be joined together, trapping the intermediate layer there between by any means such as with screws, ultrasonic welding or laser welding.

The valve chamber 190 is arranged to receive a valve shuttle bar 200 carried by and extending from the first actuator button 116. A series of O-rings, to be described subsequently, are seated on the shuttle bar 200 to form first, second, and third valves. The actuator button 116 also carries a first linkage portion 240 of the linkage that permits actuation of the device pump with the actuator control button 118 only when the second fluid path has been established by the first actuator control button 116. The first linkage portion 240 is received within a suitably configured bore 270 formed in the base layer 160 and will be described subsequently.

The pump actuator button 118 is arranged to be linked to a pump piston 300 and a second linkage portion 340 to interact with the first linkage portion 240. The pump piston 300 is arranged to be received within the pump chamber 170 and the second linkage portion 340 is arranged to be received within the bore 270 for interacting with the first linkage portion 240. O-rings are seated on the piston 300 to provide a seal against leakage and to prevent external contaminants from entering the piston chamber.

The intermediate layer 164 may be a generally resilient member and received on the base layer 160 to cover channels scribed in the base layer as a type of gasket to form fluid channels 380 that serve to conduct the medicament from the reservoir to the device outlet and to the distal end 131 (FIG. 2) of the cannula 130. Springs 410 are arranged to spring load the actuator buttons 116 and 118 away from each other.

The reservoir membrane 162 is formed of flexible membrane material and is received over the reservoir portion 168 to form the reservoir of the device 110. A rigid plate 420 is arranged to be adhered to the reservoir membrane 162 of the reservoir. Because the membrane 162 is flexible, it will move as the reservoir is filled and emptied. The rigid plate 420 will then move with it. The plate 420 includes an eyelet 422 dimensioned to receive an elongated web 424 that forms a part of a medicament level indicator. The web 424 carries an indicator line or feature 426 that may be read through a window 428 of the device top most panel 440.

Another component of the device 110 is a translucent window 450 that is received on the underside of the base 160. As will be seen hereinafter, the window forms a part of a prime indicator. It is formed of a transparent material such as glass or transparent plastic and has a roughened surface rendering it translucent. However, when it is covered with or at least wetted by liquid medicament, it is rendered essentially transparent creating a visually obvious condition and, for example, permitting indicia to be seen beneath it indicating that the conduit to the device outlet is primed and ready to deliver fixed doses of medicament when desired.

Figure 4:
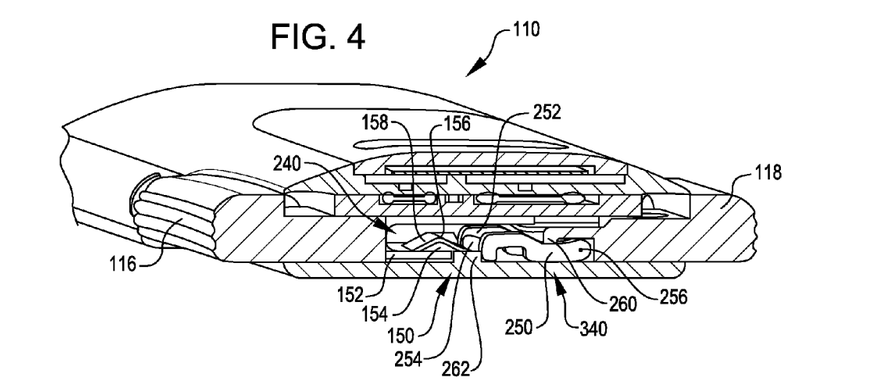
FIG. 4 is a sectional view, in perspective, to an enlarged scale, taken along lines 4-4 of FIG. 1, showing the actuation linkages of the device of FIG. 1 prior to medicament dosage delivery.
Figure 5:
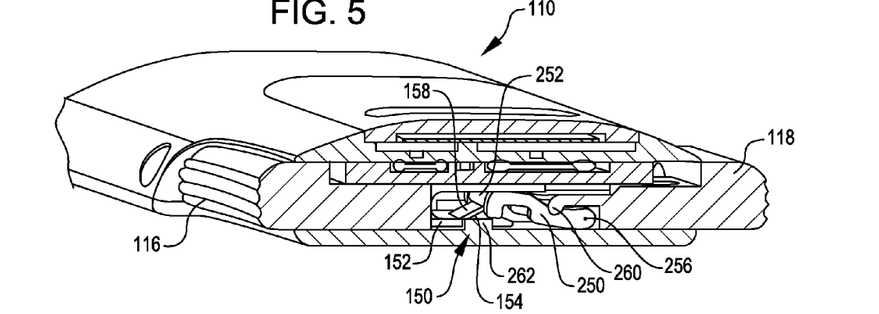
FIG. 5 is another sectional view, in perspective, to an enlarged scale, taken along lines 5-5 of FIG. 2, showing the actuation linkage operation of the device of FIG. 1 during medicament dosage delivery.
Figure 6:
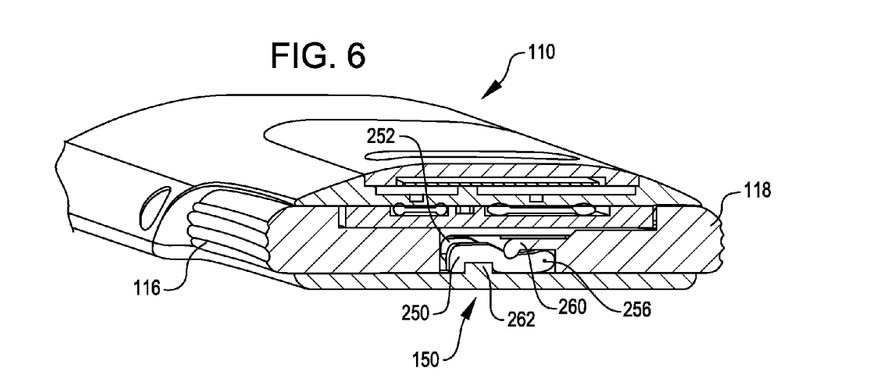
FIG. 6 is another sectional view similar to that of FIG. 5, in perspective, to an enlarged scale, showing the actuation linkage operation of the device of FIG. 1 immediately after dosage delivery.

FIGS. 4-6 show details of the operation of the linkage that permits actuation of the device pump with the actuator control button 118 only when the second fluid path from the reservoir to the outlet has been established by the first actuator control button 116. The linkage has been given the general reference character 150.

As may be seen FIG. 4, the first actuator button 116 has an extension 152 that terminates in a block 154. The block 154 has a first ramp surface 156 and a second ramp surface 158. When the device 110 is actuated, the button 116 is concurrently depressed with pump button 118. It and its extension 152 and block 154 are free to move to the right. As seen in FIGS. 4 and 5, the pump actuator button 118 has parallel extensions 250 and 252 which are joined and separated be a rod member 254. The extensions 250 and 252 are pivotally mounted to pivot about a pivot point 256. Another extension 260 of the pump actuator button 118 spring biases the extensions 250 and 252 as shown in FIG. 4. As seen in FIG. 4, the extensions 250 and 252 abut an abutment 262 which they must clear to enable the actuator 118 to be moved to the left. As shown in FIG. 5, as the button 116 is depressed, its extension 152 moves to the right causing the first ramp surface 156 to engage the rod member 254. Continued movement of the button causes the rod member 254 to ride up the first ramp surface 156 which in turn causes the extensions 250 and 252 to begin to move slightly to the left and bend upward against the loading of extension 260. Eventually, the rod member 254 rides up the length of the first ramp 156 and down the second ramp 158 causing the extensions 250 and 252 to clear the abutment 262 and continue their travel to the left until the extensions are received on the opposite side of the abutment as shown in FIG. 6. The pump button 116 has now been fully depressed to deliver a dose of measured medicament. When the ends of extensions 250 and 252 totally clear the abutment 262, they will snap behind the abutment 262 as shown in FIG. 6 and become temporarily locked. Meanwhile, the rod member 254 has traversed all the way down the second ramp surface 158. The buttons 116 and 118 are now fully depressed.

Hence, from the above, it may be seen that the pump button 118 could not at first move freely while the first actuator button 116 which operates the valves could. As a result, the pump actuation lags behind the valve actuation. This enables the device outlet to be sealed from the reservoir and the pump connected to the outlet before the pump is permitted to pump any medicament to the outlet. Hence, the device establishes a medicament delivery flow path to the cannula before the pump is able to begin pumping the medicament to the patient. Thus, it is assured that there is never an open unobstructed pathway between the reservoir and the fluid outlet. Also, by assuring that the pump only draws fluid from the reservoir when the pathway to the outlet is sealed off, it is also assured that a precise amount of fluid is moved with each pump cycle. This operation is completely timed by the linkage just described and occurs quickly, appearing to the patient that both actuator buttons are moving at the same rate.

When the extensions 250 and 252 of the pump button clear the abutment 262, they become locked in a snap action. This provides positive feedback to the patient that a dosage of medicament was delivered as desired. It also causes a full dose to be delivered. By virtue of the snap action of the pump actuator, only full doses may be administered.

When the medicament has been delivered, the spring loading of the actuator buttons returns the buttons to their first or initial position. During this time, the same timing provided by the block 154 is used for recharging the pump. More specifically, ramp 158 unlatches the ends of extensions 250 and 252 by lifting rod member 254. While the extensions 250 and 252 are being lifted by the ramp 158, the valve control button 116 is returning to the left to cause the outlet to be disconnected from the pump before the reservoir is reconnected to the pump for charging, thus sealing the outlet from both the pump and the reservoir before the reservoir is connected to the pump for recharging. This assures that the pump does not pull medicament from the patient but only from the reservoir. As the pump returns, a full dose of the medicament is drawn up into the piston chamber 170 to ready the device for the next dosage delivery.

Figure 7:
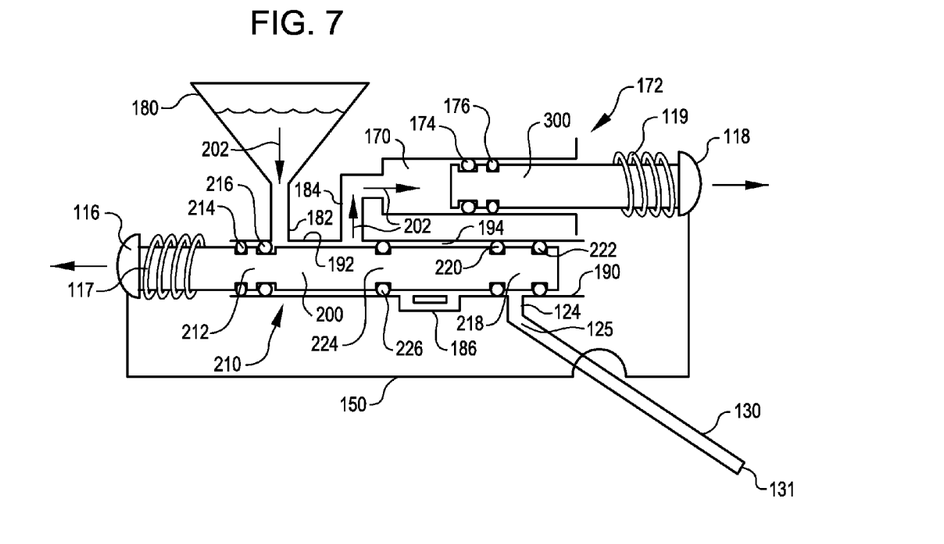
FIG. 7 is a schematic representation of the valves and pump of the device of FIG. 1 between medicament dosage deliveries and during the filling of the pump with the medicament.
Figure 8:
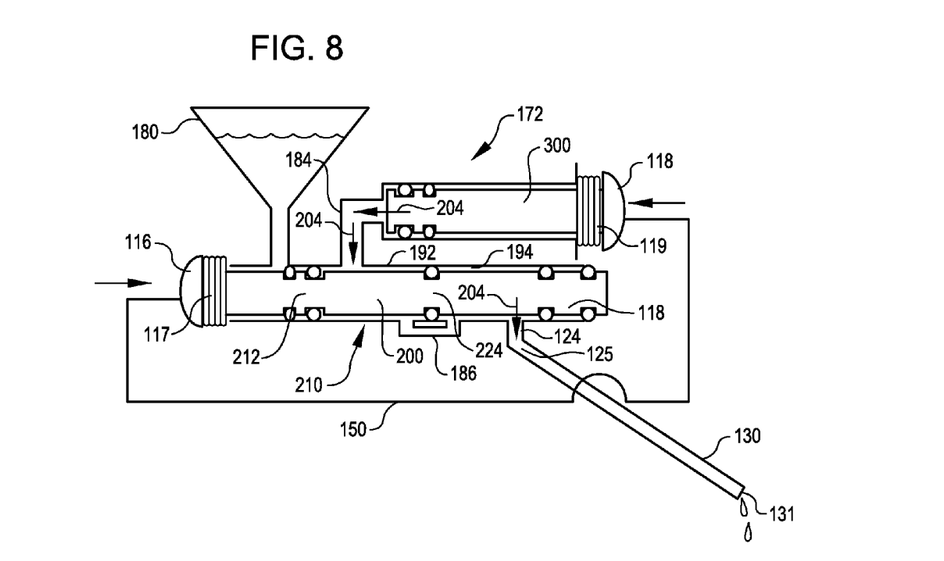
FIG. 8 is another schematic representation of the valves and pump of the device of FIG. 1 during medicament dosage delivery.

Referring now to FIGS. 7 and 8, they are schematic representations of the valves and pump of the device of FIG. 1 between medicament dosage filling (FIG. 7) and medicament dosage delivery (FIG. 8) As may be seen in FIGS. 7 and 8, the device 110 further includes a reservoir 222, a pump 224, and the cannula 130. The reservoir 222 may be formed as shown in FIG. 3 by the combination of the device base 160 and the flexible membrane 162. The device further includes the shuttle valve 210 including shuttle bar 200. The shuttle bar 200 is shown within the valve chamber 190. The shuttle bar 200 and O-rings 214 and 216 form a first valve 212, shuttle bar 200 and O-rings 220 and 222 form a second valve 234 and shuttle bar 200, O-ring 226 and a bypass channel 186 form a third valve 224. Although O-rings are used herein to form seals, other types of valve construction may employ forms of seals other than O-rings without departing from the invention.

The pump piston 300 is within the piston camber 170 to form a piston pump 172. The actuator control button 218 is directly coupled to and is an extension of the pump piston 226. It may also be noted that the actuator buttons 116 and 118 are spring loaded by springs 117 and 119, respectively. The springs are provided for returning the actuator buttons to a first or start position after a dosage is administered.

A fluid conduit 182 extends between the reservoir 180 and the valve 212. An annular conduit 192 extends between the O-rings 216 and 226, and an annular conduit 194 extends between the O-rings 226 and 220. A fluid conduit 184 provides a fluid connection between the reservoir 180 and the annular conduits 192 and 194 depending upon the position of the shuttle valve 210. Also illustrated in FIG. 7 is the linkage 150 that assures that the shuttle valve 210 is actuated before the piston pump 172 is actuated to provide a dose of medicament.

In FIG. 7, the valves are shown in a first configuration immediately after having returned to their first position following a dosage delivery. After the return of the valves, the linkage 150 permits the pump actuator 118 and piston 300 to return for refilling the pump chamber 300 in ready for the next medicament dosage delivery. During their return, the medicament flows as indicated by arrows 202 from the reservoir 180, through the conduit 182, through the annular channel 192, through conduit 184, and into the pump chamber 170.

As may be noted, when in the first position, the valves 218 and 224 isolate the outlet 124 from both the reservoir 180 and the piston pump 118. Having two such valves isolate the outlet 124 when the valves are in the first configuration provides an added degree of safety from medicament being inadvertently delivered to the patient between dosage deliveries. For example, this provides additional safety that the liquid medicament is not accidentally administered to the patient notwithstanding the inadvertent application of pressure to the reservoir. In applications such as this, it is not uncommon for the reservoir to be formed of flexible material. While this has its advantages, it does present the risk that the reservoir may be accidentally squeezed as it is worn. Because the valves 118 and 124 isolate the outlet 124 when the valves are in their first configuration, this redundant protection assures that pressure, accidentally applied to the reservoir, will not cause the fluid medicament to flow to the cannula.

In addition to the linkage 150 preventing return of the piston 300 until after the valves return to their first and start positions, the O-rings on the shuttle bar 200 are also spaced apart to insure that the valves 218 and 224 isolate the outlet 124 from the pump 172 and reservoir 180 before the pump is again connected to the reservoir. The O-ring spacing thus effectively forms a second linkage to assure that the cannula 130 is connected to the pump 172 only when a dosage is to be delivered and that it is never connected to the reservoir 180.

In operation, the pump chamber 170 is first filled as the actuator button 118 returns to the first position after having just delivered a medicament dosage. In this state, the shuttle valve 210 is set so that the first valve 212 will be open and the second and third valves 218 and 224 will be closed. This establishes a first fluid path indicated by arrows 202 from the reservoir 180 to the pump chamber 170 to fill the piston pump 172. When the patient wishes to receive another dose of medicament, the actuator buttons are concurrently pressed. The aforementioned linkages, including linkage 150, cause the first valve 212 to close and the second and third valves 218 and 224 to thereafter open. Meanwhile, actuation of the pump 172 is precluded until the first valve 212 is closed and the second and third valves 118 and 224 are opened. At this point a second fluid path indicated by arrows 204 is established from the pump chamber 170 to the cannula 130. The medicament is then administered to the patient through the distal end 131 of cannula 130.

Once the medication dosage is administered, the piston 330, and thus the actuator button 118, is returned under the spring pressure of spring 119 to its initial position. During the travel of the piston back to its first position, a given volume of the liquid medicament for the next dosage delivery is drawn from the reservoir into the pump chamber 170 as described above to ready the device for its next dosage delivery.

Figure 9:
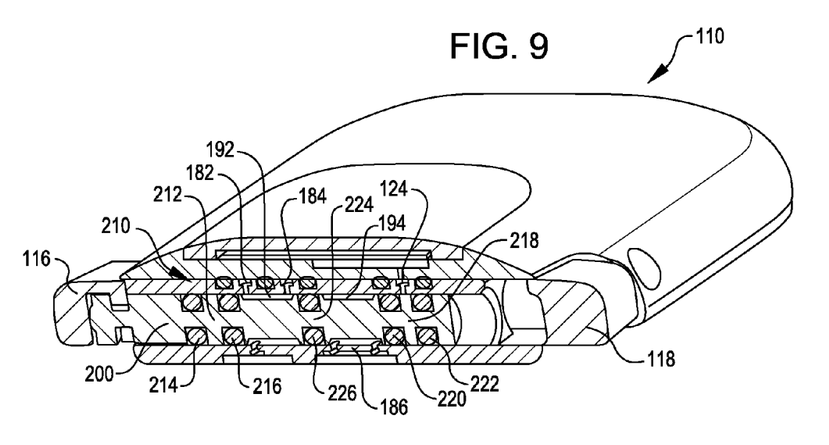
FIG. 9 is a sectional view, in perspective, to an enlarged scale, showing the configuration of the valves of the device of FIG. 1 during pump filling and prior to medicament dosage delivery.

Referring now to FIG. 9, it is a sectional view in perspective showing the valve configuration of the device 110 of FIG. 1 during medicament filling of the pump chamber 170 immediately after a dosage delivery. Here, it may be clearly seen that the first actuator button 116 is directly coupled to the shuttle bar 200 of the valves 212, 218, and 224. Above the valves are the conduits from the reservoir, from the pump, and to the cannula. More particularly, the conduit 182 is in fluid communication with the reservoir, the conduit 184 is in fluid communication with the pump, and the conduit 124 is in fluid communication with the cannula. The valves are shown with the first valve 212 opened, communicating reservoir conduit 182 with the pump conduit 184 through channel 192, the second valve 218 closed and blocking the conduit 124 to the cannula, and the third valve 224 closed and blocking both the reservoir conduit 182 and the pump conduit 184 from the cannula conduit 124. This permits medicament to flow from the reservoir through conduit 182, through channel 192, and to the pump chamber 170 through conduit 184 as the actuator button 116 returns to its first position. Hence, the pump chamber is filled and ready for the next dosage delivery.

Figure 10:
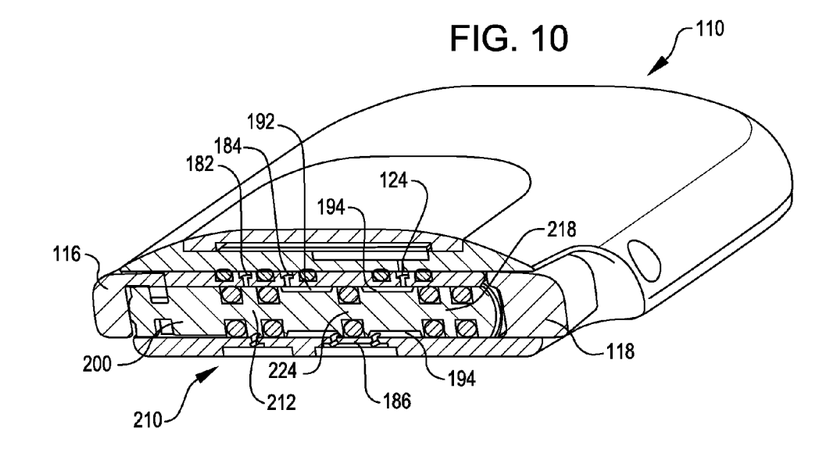
FIG. 10 is another sectional view, in perspective, to an enlarged scale, showing the configuration of the valves of the device of FIG. 1 during dosage delivery.

Referring now to FIG. 10, it is a sectional view in perspective similar to that of FIG. 9 but showing the valve configuration of the device 110 of FIG. 1 during medicament delivery. Here, the valves are shown with the first valve 212 closed and blocking the reservoir conduit 182, the second valve 218 opened permitting the outlet conduit 124 to communicate with the annular conduit 194, and the third valve 224 opened permitting medicament to flow from the annular conduit 192, through bypass 186, and to annular conduit 194. Thus, medicament is permitted to flow from the pump conduit 184, through annular conduit 192, through the bypass 186, through annular conduit 194, and into the outlet conduit 124 to administer the fixed volume dosage. As previously mentioned, the O-rings defining the first valve 212, the third valve 224, and the second valve 218 are spaced apart so that conduit 182 is blocked before conduits 184 and 124 are connected together through the valves 224 and 218.

Figure 11:
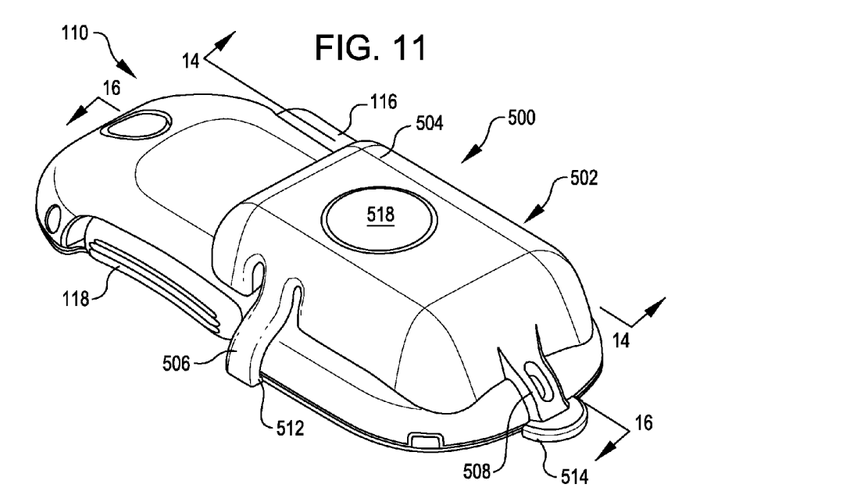
FIG. 11 is a perspective view of an infusion assembly embodying the present invention showing the infusion device of FIG. 1 and a dosage monitor releasably attached thereto in accordance with aspects of the present invention.
Figure 12:
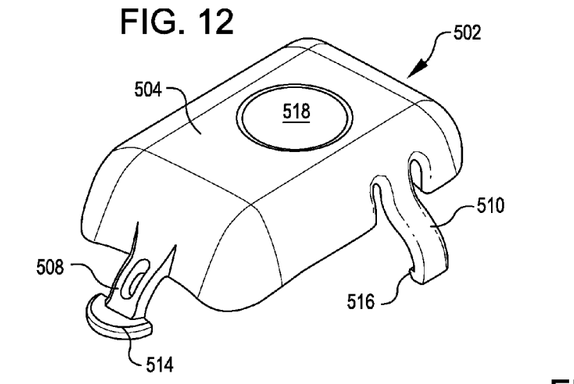
FIG. 12 is a perspective view of the dosage monitor of FIG. 11.

FIG. 11 is a perspective view of an infusion assembly 500 embodying the present invention showing the infusion device 110 of FIG. 1 and a dosage monitor 502 releasably attached thereto in accordance with aspects of the present invention. The dosage monitor 502 includes an enclosure 504. With additional reference to FIG. 12, the enclosure 502 has legs 506, 508, and 510. The legs 506, 508, and 510 are resilient and include feet 512, 514, and 516, respectively, that grip the device 110 when snap fitted thereon. The dosage monitor 502 further has a user switch button 518 that, as will be seen subsequently, when pressed, causes the monitor 502 to provide the user with information concerning drug delivery to the user by the device 110. As will also be seen, the information is delivered to the user in the form of a perceptible response. In accordance with this embodiment, the perceptible response is tactile, and more specifically, in the form of a vibration provided by an electric motor. The information delivered may be an indication of the amount of drug delivered to the used during a last dosing session.

Figure 13:
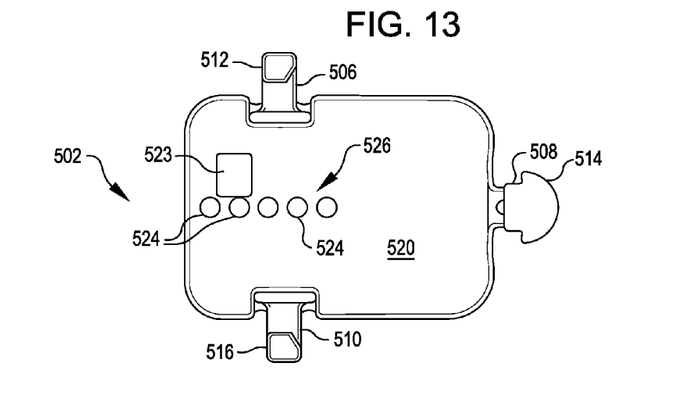
FIG. 13 is a bottom plan view of the dosage monitor of FIG. 11.

FIG. 13 is a bottom view of the monitor device 502. Here it may be seen that the monitor housing 504 has a bottom surface 520. Within the bottom 520 there is a window 523. As will be seen subsequently, the monitor 502 includes an optical sensor that senses operation of the piston pump. To that end, as will be seen subsequently, the monitor includes a light source, such as an infrared light source, that shines a beam of infrared light through the window 523 onto an extension of the piston pump actuator button 118. The extension is provided with a reflective coating that passes through the light beam during each stroke of the piston pump. During each such stroke, the infrared light is reflected back from the reflective coating to an infrared light sensor in the monitor 502 and counted. The number of such strokes during a dosing session is stored in memory for later response to a user inquiry.

In addition to storing the number of drug deliveries during a last dosing session, the monitor may also store a history of dosage deliveries. The dosing history is preferably stored in a non-volatile memory. The history data associated with the operation of the drug delivery device 110 may be transferred to an external device using a plurality of contacts 524 that form an external interface 526. The external interface 526 may be a USB interface. To that end, the interface 526 of the monitor 502 may be plugged into a USB adapter, such as a USB dongle, that converts the signals on contacts 524 to USB format to connect the monitor to an external device such as, for example, a personal computer. Alternatively, the USB formatting may be accomplished within the monitor 502 so that the signals at contacts 524 are already USB formatted. Once the monitor 502 is interfaced with the computer, the monitor may be powered through the USB port. This eliminates the need for an internal power source for this purpose. The entire contents of the monitor memory may then be downloaded to the computer to render the entire dosing history available. As may further be appreciated by those skilled in the art, the interface 526 may alternatively be coupled to a serial interface for connection to a computer.

Figure 14:
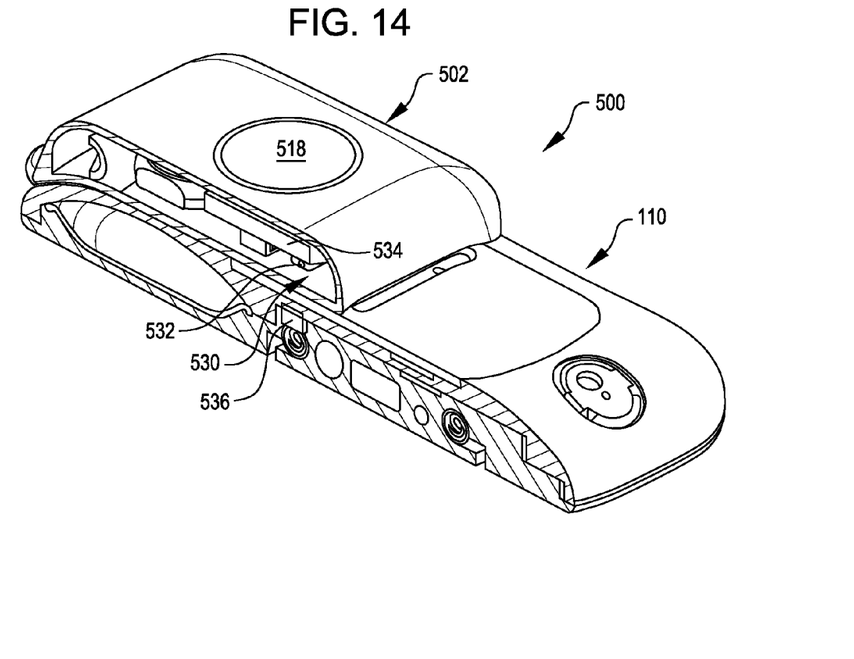
FIG. 14 is a perspective view taken along lines 14-14 of FIG. 11.
Figure 15:
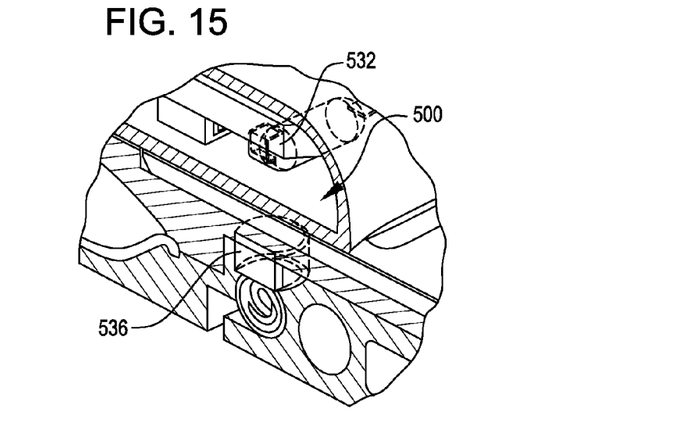
FIG. 15 shows a portion of the perspective view of FIG. 14 illustrating a magnet carried by a valve actuation button of the infusion device and a magnetic sensor of the dosage monitor in accordance with aspects of the present invention.

In addition to the optical sensor mentioned above, the sensor of the monitor 502 includes a magnetic sensor 530 which may be seen in the sectional view of FIG. 14 and the partial view of FIG. 15. The magnetic sensor 530 includes a reed switch 532 carried on a circuit board 534 of the monitor 502. The reed switch 532 is arranged to be above an extension of the first actuator button 116 (FIG. 11). As previously described, the first actuator button 116 configures a valve system for drug delivery prior to actuation of the piston pump with the second actuator button 118. The first actuator button 116 carries a magnet 536. When a drug dose is to be delivered, actuation of the first actuator button 116 causes the magnet 536 to translate beneath the reed switch 532. The reed switch 532 then closes to transition the monitor from a sleep mode to an active mode for sensing the stroke of the piston pump and counting the dosage delivery.

Figure 16:
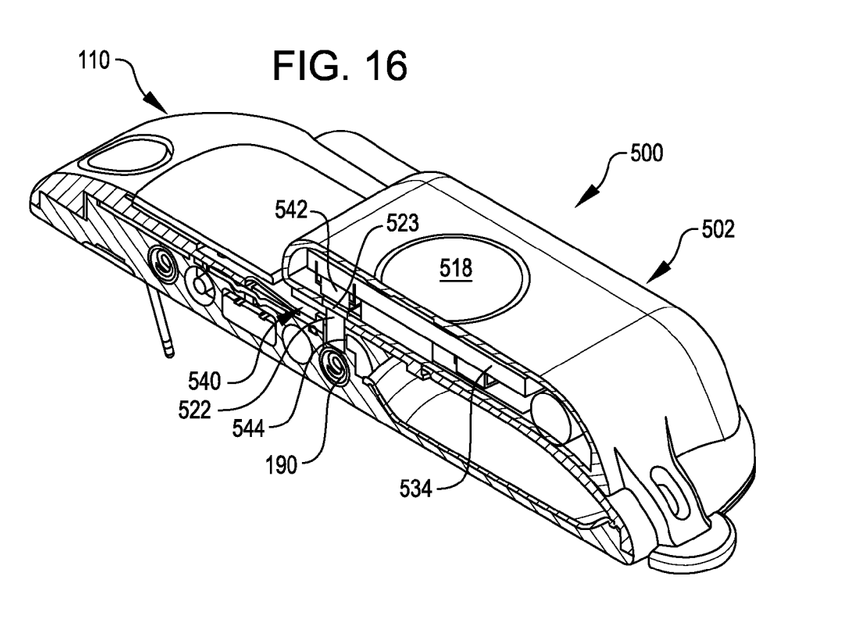
FIG. 16 is a perspective view taken along lines 16-16 of FIG. 11.
Figure 17:
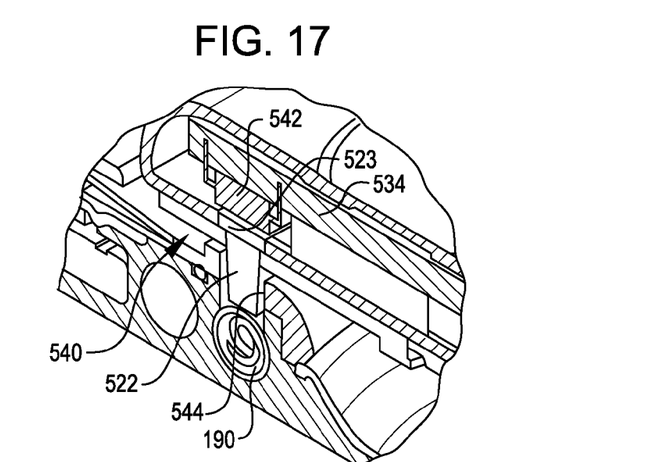
FIG. 17 shows a portion of the perspective view of FIG. 11 illustrating a reflective surface of a pump actuation button of the infusion device and a light source and an optical sensor of the dosage monitor in accordance with additional aspects of the present invention.

The sectional view of FIG. 16 and the partial view of FIG. 17 illustrate the optical sensor 540. In these views it may be seen that the optical sensor 540 includes a light source and sensor unit 542 carried on the circuit board 534 of the monitor 502. As previously mentioned, the light provided and sensed by the light source and sensor unit 542 is in the infrared portion of the spectrum. The infrared light is conducted by a light pipe 522 within a shaft 544 of the drug delivery device 110 and is directed from the window 523 into the valve chamber 190. As previously mentioned, an extension of the pump actuator button 118 carries a reflective coating that passes through the beam of light with each stroke of the piston pump. The reflected light is then returned through the light pipe 522 to the light source and sensor unit 542 to enable the counting of the piston pump stroke and thus the delivered incremental dose.

Figure 18:
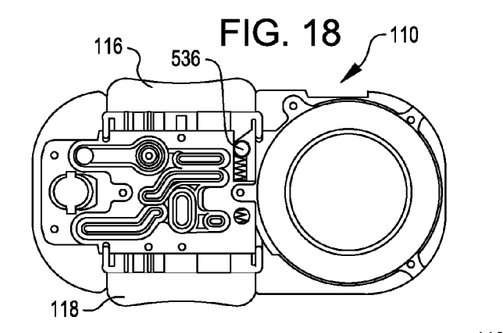
FIGS. 18-21 are bottom views, with portions cut away, illustrating the sequential operation of the actuator buttons of the infusion device for corresponding magnetic and optical sensing according to aspects of the invention.
Figure 19:
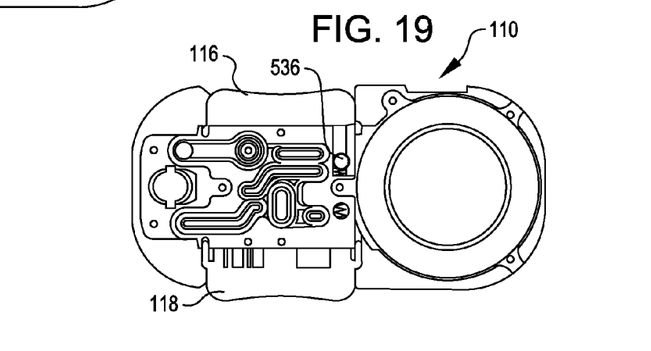

Referring now to FIGS. 18-21, they are bottom views, with portions cut away, illustrating the sequential operation of the actuator buttons of the infusion device for corresponding magnetic and optical sensing according to aspects of the invention. In FIG. 18, neither actuator button 116 nor actuator button 118 has been depressed. In FIG. 18 it may be seen that the first actuator button 116 carries magnet 536. As may be seen in FIG. 19, and as previously described, when a dose of drug is to be delivered to the user, the device 110 forces the first actuator button 116 to be depressed before the second actuator button 118 to complete required valve operation. As the actuator button 116 is depressed, the magnet 536 that it carries translates with the actuator button 116. The magnet 536 moves from its initial position shown in FIG. 18 to the position shown in FIG. 19 where it is below and in detectable proximity to the reed switch 532 (FIGS. 14 and 15). The reed switch 532 detects the magnet when the magnet field of the magnet 536 causes the reed switch 532 to close. This causes the monitor to wake from a sleep mode to prepare it for sensing the stroke of the piston pump.

Figure 20:
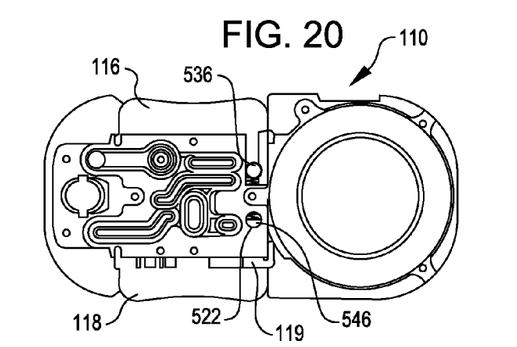
Figure 21:
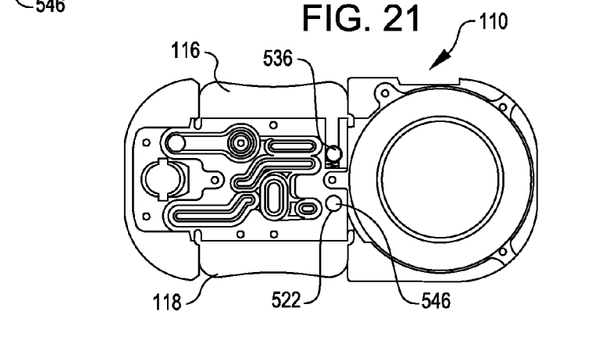

When the valve operation is completed, the second actuator button 118 is permitted to be depressed. As previously described, the forgoing actuator depressions are completed so quickly that to the user, it appears that the actuator depression of the buttons 116 and 118 is performed essentially simultaneous. FIG. 20 shows the device 110 as the actuator button 118 is being depressed. As seen in FIG. 20, the reflective coating 546 carried on the extension 119 of the actuator button 118 is viewable through the light pipe 522. In FIG. 21, all of the light pipe 522 is adjacent the reflective coating 546 to permit the light from the light source and sensor unit 542 (FIG. 17) to be conducted down the light pipe 522, reflected from the reflective coating 546, and returned to the light source and sensor unit 542 to cause the delivered incremental dose to be sensed and counted. Now, the actuator buttons 116 and 118 may be returned to their start positions as shown in FIG. 18.

Figure 22:
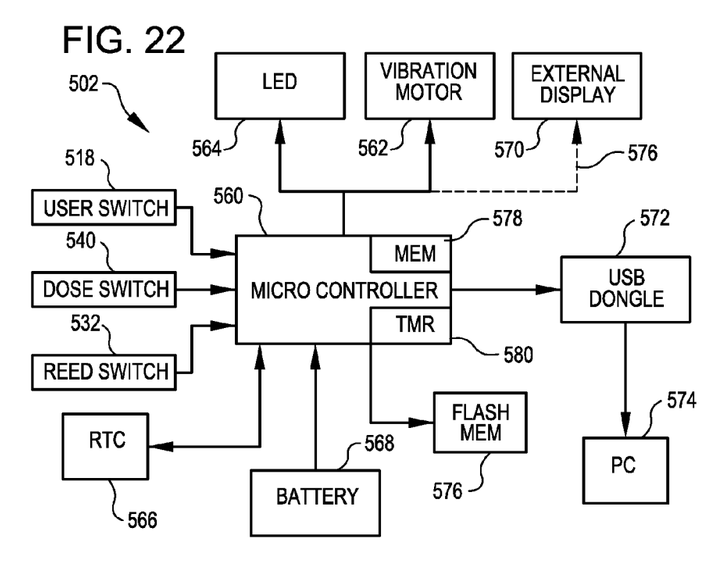
FIG. 22 is a schematic block diagram of an infusion device dosage monitor embodying the present invention.

FIG. 22 is a schematic block diagram of an infusion device dosage monitor embodying the present invention. In addition to the user switch 518, the magnetic sensor 532, and the optical sensor 540, the monitor 502 includes a microcontroller or processor 560, a vibration motor 562, a light emitting diode (LED) 564, a real time clock (RTC) 566, and a power source, such as battery 568. Also illustrated in FIG. 22 is an external display 570, a USB dongle 572, an external personnel computer (PC) 574, and a flash memory 576. The RTC 566 may, instead of being external to the processor 560, may be embedded within the processor 560.

The functions of the magnetic sensor 532, the optical sensor 540, and the user switch 518 have already been described. The processor 560 may provide all of the functionality for data acquisition, memory storage, and communication. The RTC 566 is coupled to the processor 560 to enable the processor 560 to keep time. Normally the processor 560 is maintained in a sleep mode to conserve battery power. However, the processor is responsive to interrupts to cause it to wake up and perform its functions. One such interrupt is an overflow interrupt generated by the RTC 566. This overflow interrupt occurs every 10 seconds. It causes the processor 560 to turn on and increment a seconds register by ten seconds. It then initiates an overflow check to determine if this register is at 60 seconds. If it is, a minute register is incremented and the seconds register is set to zero. In a similar process, the processor 560 checks for minute overflow for incrementing an hours register. After the hours, minutes, and seconds registers have been appropriately updated, the processor returns to sleep. The RTC overflow interrupt is preferably a high priority interrupt to supersede any other triggering event. Since only 5-10 processor clock cycles are required for this time keeping function, the processor has ample time to return to sleep and wait for other triggering events without a perceived lapse in function.

The vibration motor 563 provides a tactile response when the user requests information concerning drug delivery. The motor 562 may be provided with an offset (eccentric) weight on its output shaft to provide a perceived vibration. The information concerning the drug delivery may, in accordance with this embodiment, be the number of dosage deliveries provided during a last dosing interval timed by a timer 580 of the processor 560. To that end, the motor 563 may provide pulses of vibrations, each pulse corresponding to one dosage delivery.

The external display 570 is coupled to the processor 560 via a wireless connection 576 which may be, for example, a wifi connection. The external display 570 may be used to display a history file maintained in a processor memory 578 of the processor 560. The display may thus be a computer or other device having a wifi receiver and a display. The history file may contain the number of dosage deliveries delivered by the infusion device during each of the dosing sessions occurring over predefined period of time.

The PC 574 may be coupled to the processor 560 through the USB dongle 572. The dongle may in turn be coupled to the processor by using the USB contacts 524 (FIG. 13) arrayed on the back surface 520 of the monitor 502. The PC may also be used for displaying the history file.

The flash memory 576 may also be used to store the history file. It may be readily removable from the dosage monitor 502 and interfaced with a computer or PDA (not shown) or other similar device for displaying the history file.

Figure 23:
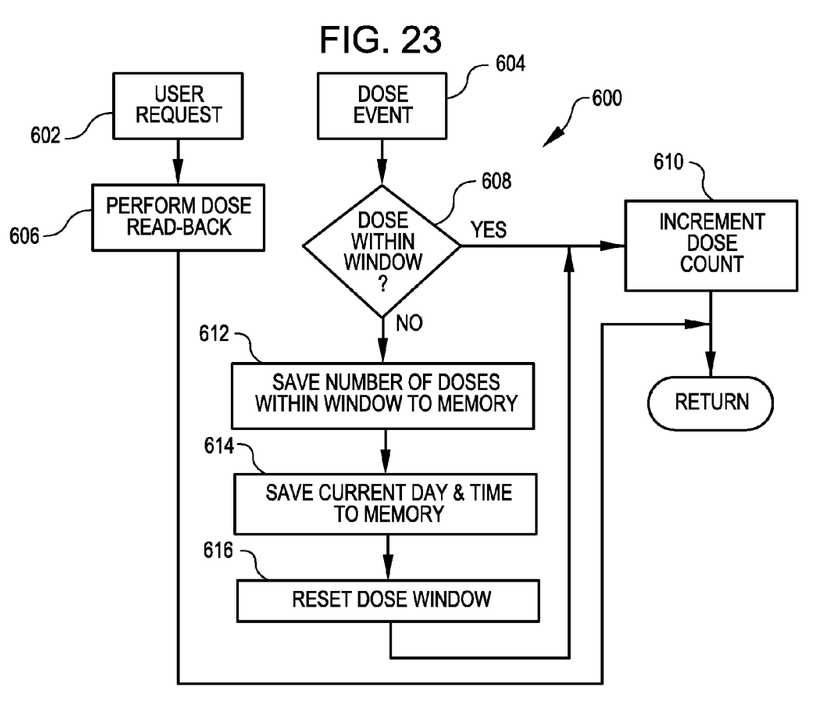
FIG. 23 is flow diagram illustrating the operation of the dosage monitor for incrementing a dosage counter and performing dosage amount read-back.

FIG. 23 is a flow diagram illustrating the operation of the dosage monitor for incrementing the dosage counter and performing dosage amount read-back. More specifically, the flow diagram of FIG. 23 shows how the processor handles interrupts other than time keeping interrupts.

The process 600 may be initiated with either the user depressing the user switch 518 (FIG. 1) as represented by activity block 602 or the user depressing the first actuator 116 as represented by activity block 604. Either event wakes the processor 560 from a power conserving sleep mode.

If the user switch has been depressed, the process advances to activity block 606 to perform the read-back. To that end, the processor will access the memory 578 to obtain the number of drug doses that have occurred in the current dosing session. The processor will then cause the motor 562 to provide a number of vibration bursts that corresponds to the number of drug doses that have been counted during the current dosing session.

If the interrupt is caused by the depression of the first actuator button 116, the process advances to decision block 608 to determine if the subsequent depression of the second actuator button 118 (FIG. 1) calling for another dosage delivery occurred during the current dosing session. If it has, the process advances to activity block 610 to increment the dose count. The process then returns and the processor falls back to sleep.

If in decision block 608 it is determined that a new dosing session has begun since the last dosage delivery request, the process advances to activity block 612 wherein the number of dosage deliveries occurring during the last completed dosing session is stored in memory for the history file. The process then advances to activity block 614 wherein the current day and time are stored in memory to time stamp the dosage delivery just administered.

The process now advances to activity block 616 wherein the timer 580 is reset for beginning the timing of a new dosing session. Once the timer 580 is reset, the process advances to activity block 610 for incrementing the dose counter. The process then returns.

The sensing of a dosage delivery as may be seen from the foregoing is a two event process. This is in response to the requirement for conserving battery power. The first event is the closing of the reed switch 532. The reed switch draws no power from the battery 568. Once the reed switch 532 is closed, the dosage delivery is validated by the optical sensor 540. The infrared optical switch has high reliability and is immune from environmental noise. Since it is an active sensing device, it is only turned on when a dosage delivery is to be validated. Hence reliable dosage delivery sensing is provided while also minimizing the power requirements for such sensing.

While particular embodiments of the present invention have been shown and described, modifications may be made, and it is therefore intended in the appended claims to cover all such changes and modifications which fall within the true spirit and scope of the invention as defined by those claims.

What is claimed is:

1. A device for providing information about the operation of a drug delivery device, the drug delivery device including a mechanical stroke pump that delivers the drug to a patient and at least one valve, the operation of which initiates operation of the drug delivery device, the device comprising:
   a mechanical stroke pump;
   a housing arranged to attach to the drug delivery device;
   a timer that times a dosing session;
   a magnetic sensor that senses the operation of the at least one valve;
   an optical sensor that senses operation of the pump to provide data indicative of each stroke of the pump;
   a memory that stores the operational data provided by the optical sensor during a last dosing session;
   an interrogator that interrogates the memory such that the memory generates a memory signal in response thereto representing each pump stroke during a last dosing session; and
   a responder that receives the memory signal and generates a tactile response.

2. The device of claim 1, further comprising
   a clock mechanism that generates a time signal
   and wherein the memory receives and stores the time signal.

3. The device of claim 1, wherein the tactile response is a vibratory response.

4. The device of claim 3, wherein the responder is a motor.

5. The device of claim 4, wherein the motor is an electric motor.

6. The device of claim 2, wherein the memory stores operational data for a number of dosing sessions in a history file.

7. The device of claim 6, further including an interface arranged to provide the history file to an external reader.

8. The device of claim 7, wherein the interface comprises a USB interface.

* * * * *